United States Patent
Rodefeld et al.

(10) Patent No.: US 6,620,962 B2
(45) Date of Patent: Sep. 16, 2003

(54) METHOD FOR PRODUCING N-BUTYRYL-4-AMINO-3-METHYL-METHYL BENZOATE AND THE NOVEL COMPOUND N-(4-BROMINE-2-METHYLPHENYL)-BUTANAMIDE

(75) Inventors: Lars Rodefeld, Leverkusen (DE); Thomas Höpfner, Neuss (DE); Alexander Klausener, Pulheim (DE); Horst Behre, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/239,678
(22) PCT Filed: Mar. 15, 2001
(86) PCT No.: PCT/EP01/02924

§ 371 (c)(1),
(2), (4) Date: Sep. 24, 2002

(87) PCT Pub. No.: WO01/72690

PCT Pub. Date: Oct. 4, 2001

(65) Prior Publication Data

US 2003/0065211 A1 Apr. 3, 2003

(30) Foreign Application Priority Data

Mar. 28, 2000 (DE) ......................... 100 15 279

(51) Int. Cl.⁷ .......................................... C07C 227/02
(52) U.S. Cl. ........................................ 560/47; 564/218
(58) Field of Search .............................. 564/218; 560/47

(56) References Cited

FOREIGN PATENT DOCUMENTS

EP           0 675 102           10/1995

OTHER PUBLICATIONS

Okuzu et al. Chem. Abst. 64:84315 (1966).*
Chem. Ber. 102, (month unavailable) 1969, pp. 2502–2507, Siegfried Huneck und Doris Meuche, "Die Synthese von 2.7–Dimethyl–5–methoxycarbonyl–inden".
Liebigs Ann. Chem. 44, (month unavailable) 1967, pp. 163–184, F. Beilstein and U. Kreusler, "Untersuchunge über Isomerie in der Benzoëreihe".
Database Chemcats Online! 19. Feb. 19, 2001 retrived from STN Database Accession No. 2001: 1202716 XP002179987 Propanamide, –(4–bomo–2–methylphenyl)–2–methyl–; RN 330469–43–7.

* cited by examiner

Primary Examiner—Peter O'Sullivan
(74) Attorney, Agent, or Firm—Godfried R. Akorli; Diderico van Eyl

(57) ABSTRACT

According to the invention, N-butyryl-4-amino-3-methyl-methyl benzoate is obtained in a particularly advantageous manner by, initially, reacting o-toluidine with butyric acid chloride, by brominating the reaction product and by reacting the bromide obtained therefrom with carbon monoxide and methanol in the presence of a palladium catalyst. The invention also relates to the important novel chemical compound N-(4-bromine-2-methylphenyl)-butanamide.

9 Claims, No Drawings

METHOD FOR PRODUCING N-BUTYRYL-4-AMINO-3-METHYL-METHYL BENZOATE AND THE NOVEL COMPOUND N-(4-BROMINE-2-METHYLPHENYL)-BUTANAMIDE

This application is a 371 of PCT/EP01/02924, filed Mar. 15, 2001.

The present invention relates to an improved process for preparing methyl N-butyryl-4-amino-3-methylbenzoate and the novel chemical compound N-(4-bromo-2-methylphenyl)butanamide.

4'-[[2-n-Propyl-4-methyl-6-(1-methylbenzimidazol)-2-yl]methyl]biphenyl-2-carboxylic acid is a valuable angio-tensin antagonist, in particular a valuable angio-tensin II antagonist (see EP-A 502 314). In the following, these carboxylic acids are also known for short as antagonists.

In J. Med. Chem. 1993, 4040 a synthesis of the antagonist is described which starts from methyl 4-amino-3-methylbenzoate (I) and reacts it with butyryl chloride to give methyl N-butyryl-4-amino-3-methylbenzoate (II) (see the following reaction scheme (1)).

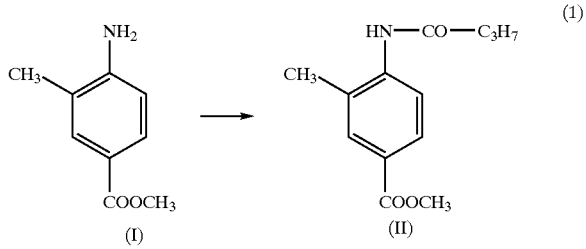

(1)

Compound (II) is then converted in further steps to the antagonist.

The required starting compound of the formula (I) is only accessible in a disadvantageous manner. For instance, 4-nitro-m-xylene (III) can be used as the starting material and converted by oxidation to 4-nitro-2-methylbenzoic acid (IV) (see Liebigs Ann. Chem. 144, 163 (1867)), which is then esterified to methyl 4-nitro-2-methylbenzoate (V) (see Chem. Ber. 102, 2502 (1969)) and reduced to methyl 4-amino-3-methylbenzoate (I) (see Chem. Ber. loc. cit.). This process for preparing compound (II) is illustrated by the following reaction scheme (2).

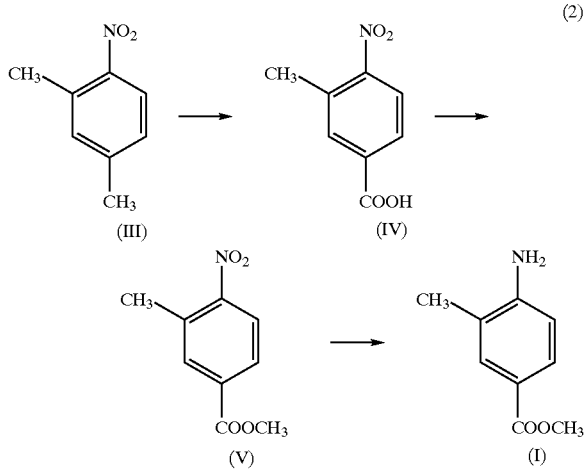

(2)

As can be seen, the known process for preparing compound (II) consists of four individual steps, and the first step (III)→(IV) is particularly disadvantageous because it requires long reaction times and leads only unselectively and therefore in low yields to (IV). According to J.O.C. 32, 134 (1967), a reaction time of 20 hours is required and the yields are from 22.5 to 27%.

There is accordingly still a need for a process for preparing compound (II) which requires fewer steps and provides compound (II) in an advantageous manner.

A process has now been found for preparing methyl N-butyryl-4-amino-3-methylbenzoate (II), which is characterized in that o-toluidine (VI) is reacted with butyryl chloride to give N-(2-methylphenyl)butanamide (VII), the latter is brominated to give N-(4-bromo-2-methylphenyl)butanamide (VIII) and this is converted by reaction with carbon monoxide and methanol in the presence of a palladium catalyst to give methyl N-butyryl-4-amino-3-methylbenzoate (II). The following reaction scheme (3) illustrates the process according to the invention.

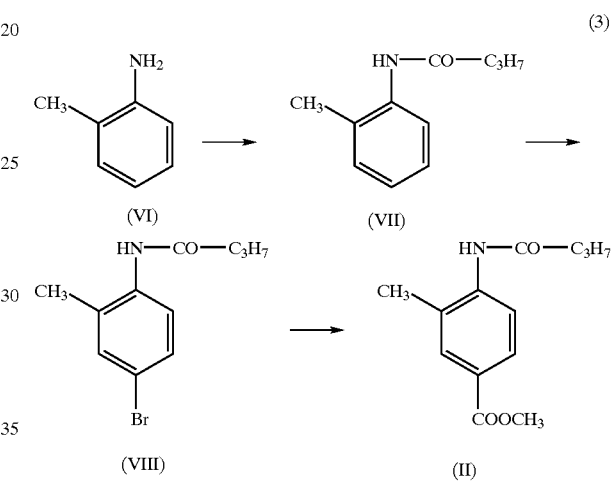

(3)

The stages (VII)→(VIII) and (VIII)→(II) are particularly surprisingly advantageous because they deliver (VIII) and (II) each in yields of over 95%.

The first stage of the process according to the invention, the reaction of compound (VI) with butyryl chloride to give compound (VII) may be carried out, for example, by initially charging compound (VI) in an inert solvent, for example an aromatic solvent such as chlorobenzene, toluene or xylene, and then metering in butyryl chloride at temperatures of, for example, 50 to 100° C. In addition to the desired compound (VII), this also results in o-toluidine hydrochloride, which can, if desired, be completely converted to the amide by further heating. The progress of the reaction can be followed via the formation of hydrogen chloride. To destroy any remaining butyryl chloride residues, methanol can be added. After cooling the reaction solution, the amide (VII) precipitates and can be isolated, for example by filtration, in a purity of generally over 98% and in yields of generally from 92 to 95%.

The second stage of the process according to the invention, the bromination of compound (VII) to compound (VIII) may be carried out, for example, by initially charging the compound (VII) in acetic acid, adding from 1 to 1.3 molar quantity of elemental bromine together with further acetic acid at from 10 to 80° C., continuing to stir the mixture at from 10 to 80° C. for from 20 minutes to 3 hours, then adding a water quantity of from 0.5 to 5 times the volume, removing the precipitate formed, washing it with water and drying it under reduced pressure. Compound (VIII), i.e. N-(4-bromo-2-methylphenyl)butanamide can be obtained in this manner in yields of generally over 95% and in purities of generally over 99%.

The third step of the process according to the invention, the conversion of compound (VIII) by reaction with carbon monoxide and methanol in the presence of a palladium catalyst to compound (II) may be carried out, for example, by initially charging the compound of the formula (VIII) and a palladium catalyst into a pressure vessel, then adding a mixture of methanol, optionally one or more solvents other than methanol and a base, then pressurizing at from 90 to 160° C. to 2–30 bar of carbon monoxide and maintaining this pressure until no more carbon monoxide is taken up.

In the third step of the process according to the invention, methanol may serve as a reaction partner and solvent. Optionally, one or more organic solvents other than methanol may additionally be used. Preferred additional organic solvents include hydrocarbons such as hexane, cyclohexane, heptane, benzene, toluene, the isomeric xylenes and mixtures thereof, chlorinated hydrocarbons such as chlorobenzene, dichlorobenzene, methylene chloride and hexachloroethane, nitriles such as acetonitrile, amides such as dimethylformamide and ethers such as dioxane and tetrahydrofuran. The use of such solvents is advantageous where it increases the solubility of carbon monoxide in the solution. This reaction stage can then be carried out at relatively low pressures, which on the industrial scale in particular is associated with lower apparatus and safety engineering demands.

The palladium catalysts used may, for example, be those of the $Pd(PPh_3)_2X_2$ type where Ph=optionally substituted phenyl and X=halogen, which may also be prepared in situ from $PdX_2$ and $PPh_3$. The triphenylphosphine component may also be added in excess. Based on compound (VIII), for example, from 0.1 to 1 mol % of palladium catalyst may be used.

Examples of useful bases include carbonates, hydrogen carbonates and acetates of alkali metals. However, preference is given to primary, secondary and tertiary amines, in particular tri-$C_1$–$C_{10}$-alkylamines. Based on 1 mol of compound (VIII), for example, from 0.9 to 5 mol, preferably from 1.05 to 2 mol, of base can be used.

The process according to the invention provides compound (II) in an only 3-step process in good yields and in good purities. The yield in the process according to the invention over all three steps is generally from 90 to 95%. This is a substantial improvement in accessibility to compound (II) and to the antagonists preparable from compound (II).

One embodiment of the process according to the invention is a synthesis of (VIII) without intermediate isolation of compound (VII). This is technically advantageous, since the intermediate isolation of a compound always requires additional apparatus, which slow the process and generally reduce the yield by isolation losses and residues, for example in mother liquors.

In this embodiment, the initial procedure is as described for preparing compound (VII). The crude solution of (VII) obtained by amidation is freed of the inert solvent after butyrylation by distillation. In order to remove remaining residues of the inert solvent, water may be added to the melt of compound (VII) and distilled off again. The crude (VII) obtained may then be admixed with a solvent suitable for bromination. This is preferably acetic acid, formic acid, propionic acid or mixtures thereof with water in any ratio and also dilute mineral acids such as sulfuric acid or just water. Bromination in an inert solvent with addition of Lewis acids, for example aluminum chloride, aluminum bromide, iron bromide, or with addition of elemental iron, is likewise possible. Particular preference is given to acetic acid and also to mixtures of acetic acid and water. Bromine is added directly to this reaction mixture at temperatures of from 10 to 130° C., preferably from 30 to 60° C. Based on 1 mol of compound (VII), from 0.9 to 1.1 mol of bromine to from 1 to 1.05 mol can be added.

Owing to the resulting hydrobromic acid, only half of the valuable bromine used can be converted. Accordingly, this embodiment contemplates using only from 0.45 to 0.95 mol of bromine for 1 mol of compound (VII) and carrying out the further bromination via reoxidation of hydrobromic acid using an oxidant, preferably hydrogen peroxide, in a quantity supplementary to 1 mol.

The bromination can also be carried out using hydrobromic acid, and adding an oxidant after its addition. For example, from 0.9 to 1.1 mol of hydrobromic acid per mole of compound (VII) and an equivalent quantity of oxidant, preferably hydrogen peroxide, can be used. If appropriate, hydrobromic acid can also be used as a solution in water. Instead of hydrobromic acid, bromides can also be used, preferably potassium bromide. Bromides can also be used as such or, for example, in aqueous solution.

A technical problem in all of the above-described syntheses is that the product (VIII) of the bromination, owing to its solubility properties, precipitates after the reaction has proceeded to from about 30 to 70% spontaneously and as a fine solid. The resulting suspension can only be stirred with difficulty. An industrial reaction can accordingly only be carried out at huge cost and inconvenience.

This problem is surprisingly solved by carrying out the bromination in the form of simultaneous metering in (with a tolerance of up to 20%, preferably from 10 to 20%, in the respective volume flow rates) of the bromine or the bromine and the oxidant on the one hand and the crude (VII), optionally a mixture of (VII) and the solvent suitable for bromination, on the other hand. The reactants may be metered into a reservoir in which a portion of the solvent suitable for bromination is present. This embodiment is likewise part of the subject matter of the process according to the invention. Preferred initial charges include mixtures of acetic acid and water in a ratio of from 0.2:0.8 to 0.8:0.2. Particularly preferred 0.25:0.75 to 0.5:0.5. The crystallization behavior was also improved by adding and also compound (VIII) (slightly soluble) to the reservoir before bromination to give a suspension.

The compound of the formula (VIII) is novel. The present invention also accordingly relates to the compound of the formula (VIII), i.e. N-(4-bromo-2-methylphenyl) butanamide. This compound can be prepared as described above. It provides the key substance in the process according to the invention for preparing the compound of the formula (II). Its discovery facilitated improved access to the compound of the formula (II) and the antagonists preparable from it.

EXAMPLES

Example 1

Synthesis of N-(2-methylphenyl)butanamide (VII)

1128.6 g of o-toluidine were initially charged in 500 ml of toluene and heated to 90° C. 134.3 g of butyryl chloride were added dropwise within 2 hours. After completed addition, the mixture was heated to reflux and stirring continued at this temperature until the end of gas formation. The mixture was cooled to 70° C., 12 ml of methanol were added and stirring was continued for an hour. To remove the methanol, the mixture was heated and 70 ml were distilled off. 300 ml of toluene were then distilled off and 400 ml of cyclohexane were added. The mixture was cooled to 10° C. and filtration gave 199.5 g (92% yield) of the product in 98% purity after drying.

Example 2

Synthesis of N-(4-bromo-2-methylphenyl) butanamide (VIII)

30 g of N-butyryl-o-toluidine and 150 g of glacial acetic acid were initially charged at 30° C. A solution of 33 g of bromine in 66 g of glacial acetic acid was added with stirring and then stirring was continued at from 25 to 30° C. for 1 hour. 300 ml of water were then added to the reaction mixture which, after continued stirring for a short time, was filtered, the crystals were washed with water and dried under reduced pressure. 42.5 g (98% yield) of N-(4-bromo-2-methylphenyl)butanamide were obtained in 99.4% purity.

| Physical data: | |
|---|---|
| Melting point: | 146 to 147° C. |
| IR spectrum: | 3275 cm$^{-1}$, 1649 cm$^{-1}$ |
| $^1$H NMR spectrum at 400 MHz: | δ = 0.93 (t, 3H), 1.62 (qt, 2H), 2.19 (s, 3H), 2.31 (t, 2H), 7.35 (m, 2H), 7.4 (s, 1H), 9.27 (s. 1H). |

Example 3

Synthesis of methyl (N-butyryl)-4-amino-3-methylbenzoate (II) Without Additional Solvent 90 g of N-(4-bromo-2-methylphenyl)butanamide (obtained according to Example 2), 1.26 g of bis (triphenylphosphin)palladium(II) chloride and 3.78 g of triphenylphosphine were initially charged in a pressure autoclave. The autoclave was closed, purged with nitrogen and an oxygen-free solution of 78 g of tributylamine in 400 ml was added. The autoclave was evacuated, then pressurized with carbon monoxide to 10 bar and heated to 130° C. The pressure was then maintained at 14 bar for 4 hours. HPLC analysis (with external standard) of the reaction mixture showed the formation of methyl (N-butyryl)-4-amino-3-methylbenzoate in a yield of 95%.

The reaction solution was then freed of catalyst by boiling with activated carbon and then admixed with 500 ml of water at 80° C. At the same time, as much methanol as possible was removed by distillation. The product precipitated and was isolated by filtration. 73.4 g of colorless crystals (88% yield) were obtained in 99.5% purity.

Example 4

Synthesis of (II) With Additional Solvents 20 g of compound (VIII) together with 0.56 g of bis (triphenylphosphine)palladium(II) chloride and 3.36 g of triphenylphosphine were initially charged in an autoclave. The autoclave was closed and purged with nitrogen. A solution of 21.7 g of tri-n-butylamine, 100 ml of methanol, 100 ml of chlorobenzene and 400 ml of toluene which had been previously degassed and was maintained under exclusion of oxygen was added. The autoclave was evacuated and heated to 120° C. At this temperature, the autoclave was pressurized with carbon monoxide to 6 bar and the batch was stirred until no more carbon monoxide was taken up. After cooling, the reaction mixture was withdrawn from the autoclave, freed of catalyst and by boiling with activated carbon. HPLC analysis gave a conversion of 84.4% at a selectivity of 93%.

Example 5

Synthesis of N-(4-bromo-2-methylphenyl) butanamide (VIII) via Bromine/Hydrogen Peroxide Bromination 260 g of toluene and 85.7 g of o-toluidine were initially charged and the solution heated to 90° C. At 85–95° C., 89.5 g of butyryl chloride were added dropwise. After the end of the addition, the dropping funnel was flushed with 86 g of toluene, then the mixture was heated to reflux and stirring was continued until gas formation had ended plus one hour of supplementary reaction time. The mixture was then cooled to 70–75° C. 8 g of methanol were added and the mixture was stirred at 75° C. for one hour. To remove methanol and toluene, the mixture was heated (110–130° C.) and they were distilled off. Toward the end of the distillation, 50 g of water were added and distilled off again, in order to remove residual toluene. The mixture was then cooled to 90° C. 850 g of acetic acid were then added and the solution cooled to 50° C. 67.1 g of bromine were then slowly added dropwise. 28.6 g of hydrogen peroxide solution were then metered in at 50° C. Stirring was continued for one hour. This gave the product in a very bulky and barely stirrable form. The suspension was added to 1500 g of water and the reactor flushed once with 500 g of acetic acid. The suspension was filtered and washed twice with 500 g of water each time. After drying, 194.3 g of compound (VIII) (95.8% yield) was obtained in a purity of 99.0%.

Example 6

Synthesis of N-(4-bromo-2-methylphenyl) butanamide (VIII) via Bromine Bromination, Simultaneous Metering in a) 3087.5 g of toluene were initially charged at 20° C. 814.2 g of o-toluidine were added. At the same time, the solution was heated to 90° C. At 85–95° C., 850.3 g of butyryl chloride were metered in within 2 hours. After the end of the metering in, the mixture was heated to reflux and stirring was continued until no more gas was formed plus one hour of post-reaction time. The mixture was then cooled to 70–75° C. 76 g of methanol were added and the mixture was stirred for an hour at 75° C. To remove the methanol and toluene, the mixture was heated (110–130° C.) and 2600 g of distillate were distilled off. Toward the end of the distillation, 475 g of water were added and distilled off again, in order to remove residual toluene. Altogether, 950 g of distillate were withdrawn. The residue was then cooled to 90° C. 3000 g of acetic acid were then added, and the reaction solution cooled to 20° C.

b) 3000 g of water, 3000 g of acetic acid and 30 g of compound (VII) were initially charged and heated to 50° C. 1225.5 g of bromine and the acetic acid solution of compound (VII) obtained according to a) were metered in simultaneously at 50° C. within 8 hours. Stirring was continued for one hour. 4000 g of water were then pumped into the reaction mixture within 2 hours which was cooled to 20° C. and stirred at 20° C. for a further hour. A suspension was transferred to a filter and filtered with suction. The product was washed with 3×2375 g of water. After drying, 1755.6 g of compound (VIII) (90.2% yield) were obtained in a purity of 99.0%.

Example 7

Synthesis of N-(4-bromo-2-methylphenyl) butanamide (VIII) via Bromine/Hydrogen Peroxide Bromination, Simultaneous Metering in a) 823.3 g of toluene were initially charged at 20° C. 217.1 g of o-toluidine were added. At the same time, the solution was heated to 90° C. At 85–95° C., 226.7 g of butyryl chloride were metered in within 2 hours. After the end of the metering in, the mixture was heated to reflux and stirring was continued until no more gas was formed plus one hour of post-reaction time. The mixture was then cooled to 70–75° C. 20 g of methanol were added and the mixture was stirred for 1 hour at 75° C. To remove the methanol and toluene, the mixture was heated (110–130° C.) and 808 g of distillate were distilled off. Toward the end of the distillation, 126 g of water were added and distilled off again, in order to remove residual toluene. Altogether, 934 g of distillate were withdrawn. The residue was then cooled to 90° C. 400 g of acetic acid were then added, and the reaction solution cooled to 20° C.

b) 933 g of water, 666 g of acetic acid and 8 g of compound (VIII) were initially charged and heated to 50° C. 161.1 g of bromine and 50% of the acetic acid solution of compound (VII) obtained according to a) were metered in simultaneously at 50° C. within 4 hours. 115.2 g of a 30% hydrogen peroxide solution were then metered in at the same temperature. After the end of the reaction, 1066 g of water were added and the mixture was cooled to 20° C. After filtration and drying, 462.7 g of compound (VIII) (80% yield) were obtained in a purity of 89.6%.

What is claimed is:

1. A process for preparing methyl N-butyryl-4-amino-3-methyl-benzoate, comprising a first step of reacting o-toluidine with butyryl chloride to give N-butyryl-2-methylaniline, a second step of brominating the N-butyryl-2-methylaniline to give N-(4-bromo-2-methylphenyl) butanamide and a third step of converting the N-(4-bromo-2-methylphenyl)butanamide by reaction with carbon monoxide and methanol in the presence of a palladium catalyst to give methyl N-butyryl-4-amino-3-methylbenzoate.

2. The process as claimed in claim 1, wherein the first step is carried out by initially charging o-toluidine in an inert solvent and then metering in butyryl chloride at temperatures of from 50 to 100° C.

3. The process as claimed in claim 1, wherein the second step is carried out by initially charging N-butyryl-2-methylaniline in acetic acid, adding from 1 to 1.3 molar quantity of elemental bromine together with further acetic acid at from 10 to 80° C., continuing to stir the mixture at from 10 to 80° C. for from 20 minutes to 3 hours, then adding a water quantity of from 0.5 to 5 times the volume, removing the precipitate formed, washing it with water and drying it under reduced pressure.

4. The process as claimed in claim 1, wherein the third step is carried out by initially charging N-(4-bromo-2-methylphenyl)butanamide and a palladium catalyst into a pressure vessel, then adding a mixture of methanol, optionally one or more solvents other than methanol and a base, then pressurizing at from 90 to 160° C. to 2–30 bar of carbon monoxide and maintaining this pressure until no more carbon monoxide is taken up.

5. The process as claimed in claim 1, wherein the palladium catalysts used are those of the $Pd(P\ Ph_3)_2X_2$ type where Ph is optionally substituted phenyl and X is halogen.

6. The process as claimed in claim 1, wherein a base is added in the third stage.

7. A process for preparing N-(4-bromo-2-methylphenyl) butanamide, comprising initially charging o-toluidine in an inert organic solvent, metering butyryl chloride in at temperatures of from 50 to 100° C., removing the solvent by adding water to the melt of the amide obtained and distilling it off again, admixing the crude amide thus obtained with a solvent suitable for bromination and adding from 0.45 to 0.95 of bromine per mole of the amide at temperatures of from 10 to 130° C. and, to supplement to 1 mol, an oxidant.

8. A process for preparing N-(4-bromo-2-methylphenyl) butanamide, wherein butyryl chloride is metered into o-toluidine at from 50 to 100° C., the solvent is removed distillatively, and water is optionally added to the melt of the amide obtained and distilled off again.

9. The process as claimed in claim 7, wherein the bromination is carried out by simultaneously metering in the bromine and the oxidant on the one hand and the amide on the other hand with a tolerance of up to 20% in the respective volume flow rates.

* * * * *